United States Patent
Colakyan et al.

(10) Patent No.: US 9,611,493 B2
(45) Date of Patent: Apr. 4, 2017

(54) METHOD FOR BIOMASS HYDROLYSIS

(71) Applicant: Renmatix, Inc., King of Prussia, PA (US)

(72) Inventors: Manuk Colakyan, Ardmore, PA (US); Ferhan Kayihan, Tacoma, WA (US)

(73) Assignee: Renmatix, Inc., King of Prussia, PA (US)

( * ) Notice: Subject to any disclaimer, the term of this patent is extended or adjusted under 35 U.S.C. 154(b) by 380 days.

(21) Appl. No.: 13/956,714

(22) Filed: Aug. 1, 2013

(65) Prior Publication Data

US 2015/0037846 A1     Feb. 5, 2015

(51) Int. Cl.
| | |
|---|---|
| *C12P 19/00* | (2006.01) |
| *C12P 19/12* | (2006.01) |
| *C13K 13/00* | (2006.01) |
| *C12P 19/02* | (2006.01) |
| *C12P 19/14* | (2006.01) |

(52) U.S. Cl.
CPC ............... *C12P 19/02* (2013.01); *C12P 19/14* (2013.01); *C13K 13/002* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 3,972,775 A | 8/1976 | Wilke et al. .................. 435/99 |
| 5,366,558 A | 11/1994 | Brink | |
| 5,597,714 A | 1/1997 | Farone et al. ................ 435/100 |
| 6,022,419 A * | 2/2000 | Torget et al. ................... 127/37 |
| 2009/0218055 A1 | 9/2009 | Uusitalo et al. | |
| 2010/0048884 A1* | 2/2010 | Kilambi ......................... 536/56 |
| 2011/0144359 A1* | 6/2011 | Heide et al. .................. 549/489 |
| 2011/0165643 A1 | 7/2011 | Retsina et al. | |
| 2012/0055466 A1 | 3/2012 | Cotti Comettini et al. | |
| 2012/0107920 A1* | 5/2012 | Taneda .................... C12P 19/14 435/276 |
| 2012/0111514 A1 | 5/2012 | Dottori et al. | |
| 2012/0122162 A1 | 5/2012 | Romero et al. | |
| 2012/0264873 A1* | 10/2012 | Eyal ......................... C12P 7/10 524/560 |
| 2012/0291774 A1 | 11/2012 | Kilambi et al. | |
| 2012/0301939 A1 | 11/2012 | Harvey et al. | |
| 2014/0017732 A1* | 1/2014 | Lane et al. .................... 435/99 |

FOREIGN PATENT DOCUMENTS

WO     2013006856     1/2013

OTHER PUBLICATIONS

Written Opinion and International Search Report issued May 12, 2014 for International Patent Application No. PCT/US2013/053197, which was filed on Aug. 1, 2013 and published as WO/2015/016930 on Feb. 5, 2015 (Inventor—Colakvan//Applicant—Renmatix, Inc.// (13 pages).

* cited by examiner

*Primary Examiner* — Taeyoon Kim
*Assistant Examiner* — Srikanth Patury
(74) *Attorney, Agent, or Firm* — Travis B. Gasa; Andrew G. Bunn; Ballard Spahr LLP

(57) ABSTRACT

Methods and systems for biomass hydrolysis are disclosed. The methods use wash liquor in a sequencing process to maximize sugar yields, particularly $C_5$ saccharides.

40 Claims, 9 Drawing Sheets

METHOD FOR BIOMASS HYDROLYSIS

FIELD OF THE INVENTION

The present invention generally relates to methods for biomass hydrolysis. More particularly, it relates to methods for biomass hydrolysis that maximize sugar yields, including $C_5$ saccharides.

BACKGROUND OF THE INVENTION

There has been increasing interest in converting cellulosic biomass to fuels or other chemicals. There are many known biomass conversion processes, including acid hydrolysis, enzymatic hydrolysis, and gasification. One biomass conversion process gaining traction is hydrothermal treatment, which typically includes a first step of contacting a biomass with hot compressed water, with or without an acid catalyst. This step enables the extraction and hydrolysis of hemicelluloses and, in some instances where a catalyst is used, the hydrolysis of cellulose to sugars. Depending on the time and temperature of the treatment, and the catalyst loading (if used), the sugars are either partially or completely extracted. Subsequent steps may include further treatment of the remaining unconverted biomass, as well as transformation of the extracted sugars from the first step into ethanol or other useful chemicals.

In the first step of this process, hemicellulose is converted to monomeric and oligomeric sugars, such as xylose, xylo-oligosaccharides, rhamnose, arabinose, galactose, and mannose. When acid is used in the first step, or if a subsequent cellulose hydrolysis step is employed, the cellulose can be converted largely to glucose and its oligomers (gluco-oligosaccharides). The ratio of oligomers-to-monomers varies depending on the severity of the reaction (e.g., the time and temperature history, and the catalyst amount, if used). The reaction also generates by-products, such as acetic acid, furfural, hydroxylmethyl furfural (HMF), and organic acids, such as formic acid and lactic acid.

Extracting the hemicellulose in this first step may include a digester that is adapted from the pulp and paper industry. Digesters used in the pulping industry are either large vessels in which wood chips are processed at batch-scale, or vertical vessels in which there is continuous downward movement of wood chips for processing. In some facilities, horizontal digesters with internal mechanisms for moving the biomass are also used. In the vertical digesters, the solid movement can be facilitated by a hydraulic head (hydraulic digesters) or by steam pressure (vapor phase). The vertical digesters usually have two zones to accomplish the overall task. In the zone at the top portion of the vertical digester, the biomass (e.g., wood chips) and water both move downward co-currently. In the lower zone at the bottom portion of the digester, the chips move downward, and fresh "wash" water is introduced at the bottom and flows towards the top of the digester, counter-currently to movement of the chips. The chips ultimately leave through the bottom of the digester, whereas the upper zone and lower zone liquid "extracts" are removed from middle of the digester. The hydrolysis of hemicellulose (and cellulose when specific catalysts are employed) to their respective oligomers and monomers occurs within the wood chip in the upper portion of the digester. The sugars and the by-products thus formed need to diffuse out from the chip to the surrounding extract. This may be accomplished in the "wash" or the diffusion section at the bottom of the column.

In the pulp and paper industry, the digesters are designed to extract the hemicellulose and most of the lignin from the lignocellulosic biomass by the addition of a catalyst, leaving most of the cellulose behind for pulping. Typically no measures are taken to maximize the yield of sugars extracted. The yield of sugars can be defined the following fashion:

$$\text{yield} = \frac{\text{mass of sugar monomer} + \text{mass of sugar oligomer}}{\text{equivalent mass of total sugars in biomass}} \times 100$$

And, as an example more specifically for xylose, the major component of hemicellulose:

$$\text{yield}_{xylose} = \frac{\begin{array}{c}\text{mass of xylose monomer }(C5) + \\ \text{mass of xylose oligomers }(C5)\end{array}}{\text{mass of total xylan in biomass} \times 1.13} \times 100$$

For processes intended for sugar production, specifically for sugars generated from hemicellulose (such as xylan), this yield needs to be maximized, especially for economic reasons. It may be possible to design a continuous digester to maximize this sugar yield, but there are attendant trade-offs, including, but not limited to, capital and engineering expenses, complicated process initiation/termination, operation complications, time to process stabilization, and unsuitability for varying amounts, types, and forms of biomass.

To overcome cost issues, smaller pulp and paper operations have used batch digesters. As mentioned above, the main goal for these operations is to delignify the biomass and make pulp, and not maximize sugars or hemicellulose extraction. A batch reactor may be used to extract lignin and hemicellulose for pulping purposes. Unfortunately, regardless of the severity of the reaction, batch reactors inherently do not maximize sugars yield, especially in situations where a catalyst is not used. For wood chips and for most forms of biomass, there will always be residual sugars trapped in the biomass, and the sugars can degrade throughout the reaction. This deficiency could be partially overcome by pressing the sugars out of biomass particles. However, a significant amount of sugars is still left behind in the biomass.

Thus, there is an ongoing need for methods for maximizing sugar yields from biomass hydrolysis. The methods of the present invention are directed toward these, as well as other, important ends.

SUMMARY OF THE INVENTION

Accordingly, in one embodiment, the invention is directed to a method comprising, consisting of, or consisting essentially of, in a processing cycle:

forming a mixture comprising fresh water and a first fresh biomass;

heating the mixture at a first temperature and a first pressure for a first time period, thereby forming a first liquid fraction and a first solid fraction;

redirecting at least a portion of the first liquid fraction from the first solid fraction,
  wherein the first liquid fraction comprises a product composition; washing the first solid fraction with a first wash liquor;
  optionally, wherein the first wash liquor comprises a wash liquor from a previous processing cycle;

wherein the washing comprises heating the first solid
fraction and the first wash liquor at a second temperature and a second pressure for a second time period,
thereby forming a second wash liquor and a second
solid fraction;
removing at least a portion of the second wash liquor from
the second solid fraction; and
repeating the processing cycle using a second fresh biomass in place of the first fresh biomass.

In another embodiment, the invention is directed to a
method comprising, consisting of, or consisting essentially
of, in a processing cycle:
forming a mixture comprising a first fresh biomass and a
first wash liquor;
optionally, wherein the first wash liquor comprises a wash
liquor from a previous processing cycle;
heating the mixture at a first temperature and a first
pressure for a first time period, thereby forming a first liquid
fraction and a first solid fraction;
redirecting at least a portion of the first liquid fraction
from the first solid fraction,
wherein the first liquid fraction comprises a product
composition; washing the first solid fraction with fresh
water;
wherein the washing comprises heating the first solid
fraction and the fresh water at a second temperature and
a second pressure for a second time period, thereby
forming a second wash liquor and a second solid
fraction;
removing at least a portion of the second wash liquor from
the second solid fraction; and
repeating the processing cycle using a second fresh biomass in place of the first fresh biomass.

In other embodiments, the invention is directed to a
system, comprising, consisting of, or consisting essentially
of:
a batch digester, comprising:
a first end;
a second end;
a heating device;
a wash liquor tank in fluid communication with the first
end of the batch digester;
a product tank in fluid communication with the second
end of the batch digester; and
a press in fluid communication with the second end of the
batch digester.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
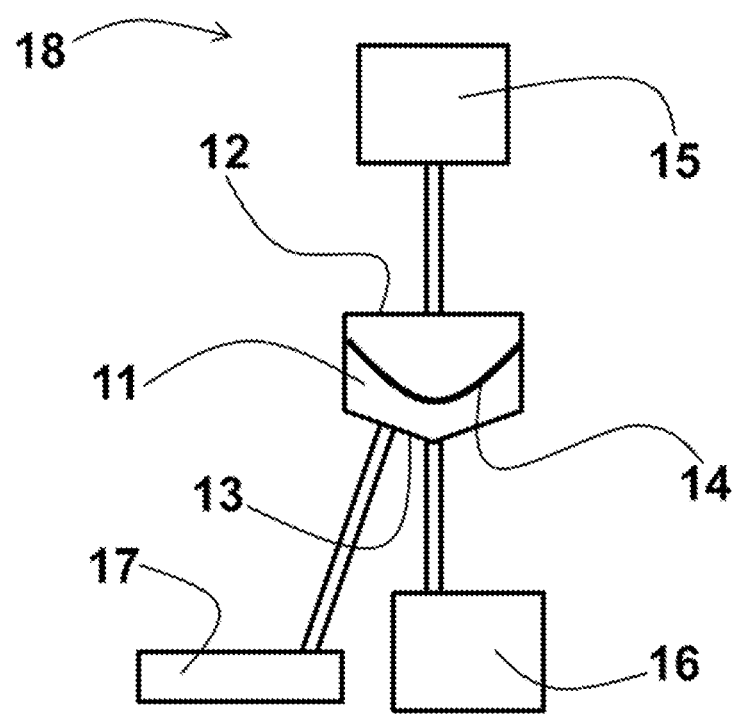
FIG. 1 is a schematic diagram showing one embodiment of a system of the invention.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250 DC and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (e.g., above about 100° C., above about 150° C., or above about 200° C.) but less than subcritical, and at pressures such that water is in a liquid state.

As used herein, a fluid which is "supercritical" (e.g. supercritical water, supercritical $CO_2$, etc.) indicates a fluid which would be supercritical if present in pure form under a Liven set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, the term "biomass" means a renewable energy source generally comprising carbon-based biological material derived from recently-living organisms. The organisms may have been plants, animals, fungi, etc. Examples of biomass include without limitation wood, lignocellulosic biomass, waste feedstocks, manufacturing waste (wood residues such as sawmill and paper mill discards), agricultural residues (including corn stover, sugarcane bagasse, rice hulls, oat hulls, etc.), food waste, plastic, black liquor (a byproduct of wood pulping processes), etc. Wood can be, for example, hardwood, softwood, annual fibers, and combinations thereof. Biomass typically comprises cellulose, hemicellulose, and lignin. Any suitable type of biomass can be used as a feedstock for the invention described herein. Starch or any other type of natural or synthetic polymer or oligomer may also be used in the inventive process. Fossil fuels are generally not considered biomass even though ultimately derived from carbon-based biological material. The term "biomass" as used herein does not include fossil fuel sources.

As used herein, the term "fresh biomass" means biomass, as defined herein, that has not been subjected to at least one processing cycle of a method of the invention. In some embodiments, "fresh biomass" means biomass that has not had at least a portion of hemicellulose removed therefrom. In some embodiments, "fresh biomass" means biomass that has not been chemically or hydrothermally treated in any way. Biomass that has been mechanically size reduced by way of, for example, cutting, grinding, milling, or the like, is considered to be "fresh biomass."

As used herein, "dry biomass" (or equivalently "bone dry biomass") refers to biomass without a moisture content (i.e., 0% moisture content). Dry biomass is typically referred to in the context of a water to dry biomass weight ratio.

As used herein, the phrase "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including sawmill and paper mill discards), and (4) municipal waste, and their constituent parts including without limitation, lignocellulose biomass itself, lignin, $C_6$ saccharides (including cellulose, cellobiose, $C_6$ oligosaccharides, $C_6$ monosaccharides, and $C_5$ saccharides (including hemicellulose, $C_5$ oligosaccharides, and $C_5$ monosaccharides).

As used herein, "oligosaccharide" refers to linear or branched carbohydrate molecules of the same or different monosaccharide units joined together by glycosidic bonds having the general formula of $C_x(H_2O)_y$, where x is about 2 to about 200. Oligosaccharides can be thought of as shorter chain polysaccharides, i.e., polysaccharides simply having less monomers in the polymeric chain. When an oligosaccharide is composed of $C_6$ monosaccharides, the general formula of an oligosaccharide can be represented as $(C_6H_{10}O_5)_n$, where n is about 2 to about 30 (i.e., the number of hexose monomers in the oligosaccharide).

As used herein, "monosaccharide" refers to any of the class of sugars that cannot be hydrolyzed to give a simpler sugar. Monosaccharides typically are $C_5$ (e.g., xylose) and $C_6$ sugars (e.g., glucose), but may also include monosaccharides having other numbers of carbon, such as $C_2$, $C_3$, $C_4$, $C_7$, $C_8$, and so on.

As used herein, "continuous" indicates a process that is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "batch" indicates a process that is carried out in one or more stages. For example, a batch process that employs a batch reactor (e.g., a batch vessel or batch digester) can be carried out in a stage, where various components are charged to the vessel, and then substantially no material is added or removed from the vessel throughout the cycle (e.g., heating or washing).

As used herein, "xylose equivalent" means the mass of xylan (and/or xylo-oligosaccharides) expressed as its equivalent mass as xylose. In other words, the "xylose equivalent" is the mass of xylose that would result from hydrolyzing xylan (and/or xylo-oligosaccharides), which accounts for the mass added from the addition of water in the hydrolysis.

As used herein, "heating" typically comprises subjecting a mixture of biomass solids (e.g., fresh biomass) and a liquid (e.g., water) to heat, such that a component (e.g., hemicellulose) of the biomass is preferentially removed.

As used herein, "washing" typically comprises washing or rinsing biomass solids that have already been subjected to at least one treatment process (e.g., a treatment process in which at least a portion of the hemicellulose present in the biomass has already been removed from the biomass). In this way, "washing" is different from "heating," as defined herein.

As used herein, "fresh water" refers to water that is substantially free of lignocellulosic biomass or a component part thereof, as defined herein. "Fresh water," as used herein, specifically excludes a wash liquor, especially a wash liquor from a prior processing cycle or a wash liquor containing any lignocellulosic biomass hydrolysate. Furthermore, "fresh water" typically does not disrupt the structure of biomass, other than through the autohydrolysis of hemicellulose (via the application of heat and/or pressure).

As used herein, a "wash liquor" refers to a liquid that does not consist of fresh water, as defined elsewhere herein. Typically, a wash liquor is a liquid that comprises biomass hydrolysate (including, but not limited to, $C_5$ saccharides, $C_6$ saccharides, glucose, gluco-oligosaccharides, xylose, xylo-oligosaccharides, and the like). Typically, a wash liquor is the liquid obtained from washing or rinsing biomass solids that have already been subjected to at least one treatment process (e.g., a treatment process in which at least a portion of the hemicellulose present in the biomass has already been removed from the biomass, and, in some embodiments, has become a component of the wash liquor). A wash liquor may include wash liquor from a processing cycle of the invention (e.g., a previous processing cycle), and/or wash liquor from another process that is not a processing cycle of the invention. The wash liquor may be used in the processing cycle of the invention in either undiluted form or diluted form. When the wash liquor is used in diluted form, the wash liquor may be diluted with another liquid, such as fresh water. In some embodiments, exogenous catalysts (e.g., acids) or other chemicals may be added to the wash liquor.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

Accordingly, in one embodiment, the invention is directed to a method comprising, in a processing cycle:

forming a mixture comprising fresh water and a first fresh biomass;

heating the mixture at a first temperature and a first pressure for a first time period, thereby forming a first liquid fraction and a first solid fraction;

redirecting at least a portion of the first liquid fraction from the first solid fraction, wherein the first liquid fraction comprises a product composition; washing the first solid fraction with a first wash liquor;

optionally, wherein the first wash liquor comprises a wash liquor from a previous processing cycle;

wherein the washing comprises heating the first solid fraction and the first wash liquor at a second temperature and a second pressure for a second time period, thereby forming a second wash liquor and a second solid fraction;

removing at least a portion of the second wash liquor from the second solid fraction; and repeating the processing cycle using a second fresh biomass in place of the first fresh biomass.

Figure 2:
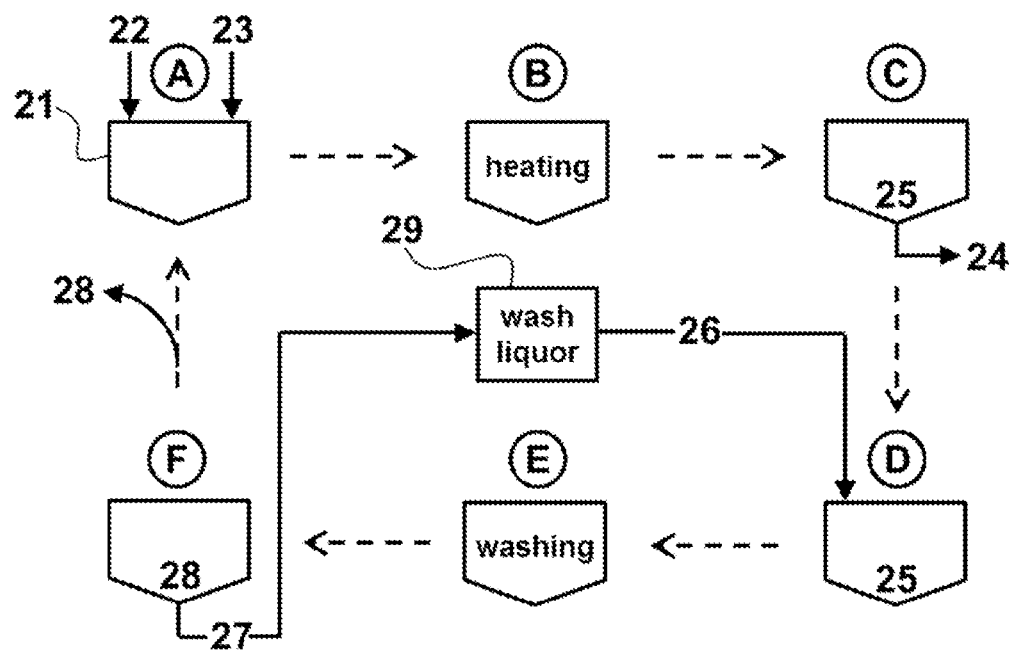
FIG. 2 is a schematic diagram showing an embodiment of a method of the invention.

A representative embodiment of this method is shown schematically in FIG. 2. FIG. 2 depicts a single vessel undergoing multiple steps, in which each step is separated by a dashed arrow (i.e., multiple vessels are not shown in FIG. 2). Solid arrows indicate material being added or removed. As shown in FIG. 2, in Step A, a first fresh biomass (22) is combined with fresh water (23) in a vessel (21) (e.g., a batch digester) to form a mixture. The mixture is then heated in Step B (i.e., "heating") at a first temperature and a first pressure for a first time period, thereby forming a first liquid fraction and a first solid fraction. In Step C, at least a portion of the first liquid fraction (24) is redirected from the first solid fraction (25). This redirection typically removes the first liquid fraction (24) from vessel (21), leaving behind the first solid fraction (25) in the vessel. The first liquid fraction (24) comprises a product composition that may be comprised of $C_5$ saccharides, as described elsewhere herein. In Step D, a wash liquor (26) is added to vessel (21) which still contains the first solid fraction (25). The first wash liquor (26) may be derived from the second wash liquor (27) that is withdrawn from the vessel (21) in Step F (discussed hereinbelow), although alternatively or additionally the first wash liquor (26) may be a liquid comprising biomass hydrolysate derived from a different process (not shown). This first wash liquor (26) may be used in the subsequent washing cycle in undiluted form, or the first wash liquor (26) may comprise wash liquor that has been combined with fresh water (not shown) to dilute the wash liquor. If using fresh water to dilute the wash liquor, the fresh water can be added before, after, or simultaneously with the addition of the wash liquor. In some embodiments, the first liquid fraction (24) is withdrawn from vessel (21) while simultaneously filling the vessel with the first wash liquor (26) (or a wash liquor). In some embodiments, while the first liquid fraction (24) is being withdrawn and the wash liquor is being simultaneously added, the wash liquor flow may be switched to fresh water to fill at least a portion of (or all of) the remaining volume in the vessel. Alternatively, or additionally, another liquid comprising biomass hydrolysate may be added to the vessel during, or after, withdrawing the first liquid fraction (24). In some embodiments, substantially no mixing occurs between the first liquid fraction and the wash liquor during the simultaneous withdrawing of the first liquid fraction and filling with the wash liquor. In some embodiments, at least some mixing occurs during the simultaneous withdrawing and filling. In some embodiments, the wash liquor, and optional fresh water, comprise the first wash liquor. In Step E (i.e., "washing"), the first solid fraction (25) is washed with a first wash liquor (26). The washing typically comprises heating the first solid fraction (25) and the first wash liquor (26) at a second temperature and a second pressure for a second time period, thereby forming a second wash liquor and a second solid fraction. In Step F, at least a portion of the second wash liquor (27) is removed from the second solid fraction (28) and may become at least a portion of the first wash liquor (26) that is used in Step D. The second wash liquor (27) may be stored in a "wash liquor tank" (29) prior to being used for washing, or the second wash liquor (27) may be fed directly into the vessel during filling Step D, as desired. The second solid fraction (28) may be expelled from the vessel by any suitable means before repeating the processing cycle using a second fresh biomass in place of the first fresh biomass. In some embodiments, the solid fraction (28) is subjected to the processing cycle at least one more time, with or without the addition of fresh biomass.

In another embodiment, the invention is directed to a method comprising, in a processing cycle:

forming a mixture comprising a first fresh biomass and a first wash liquor;

optionally, wherein the first wash liquor comprises a wash liquor from a previous processing cycle;

heating the mixture at a first temperature and a first pressure for a first time period, thereby forming a first liquid fraction and a first solid fraction;

redirecting at least a portion of the first liquid fraction from the first solid fraction,
wherein the first liquid fraction comprises a product composition; washing the first solid fraction with fresh water;
wherein the washing comprises heating the first solid fraction and the fresh water at a second temperature and a second pressure for a second time period, thereby forming a second wash liquor and a second solid fraction;

removing at least a portion of the second wash liquor from the second solid fraction; and repeating the processing cycle using a second fresh biomass in place of the first fresh biomass.

Figure 3:
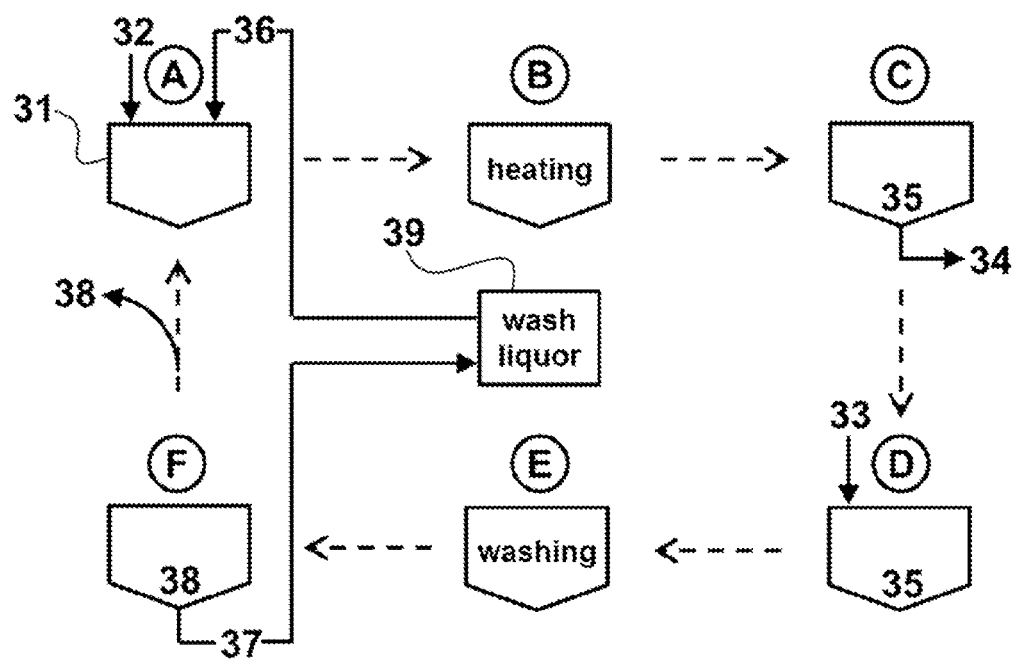
FIG. 3 is a schematic diagram showing an embodiment of a method of the invention.

A representative embodiment of this method is shown schematically in FIG. 3. FIG. 3 depicts a single vessel undergoing multiple steps, in which each step is separated by a dashed arrow (i.e., multiple vessels are not shown in FIG. 3). Solid arrows indicate material being added or removed. As shown in FIG. 3, in Step A, a first fresh biomass (32) is combined with a first wash liquor (36) in a vessel (31) (e.g., a digester) to form a mixture. The first wash liquor (36) may be derived from the second wash liquor (37) that is withdrawn from the vessel (31) in Step F (discussed hereinbelow), although alternatively or additionally the first wash liquor (36) may be a liquid comprising biomass hydrolysate derived from a different process (not shown). This first wash liquor (36) may be used in the subsequent heating cycle in undiluted form, or the first wash liquor (36) may comprise wash liquor that has been combined with fresh water (not shown) to dilute the wash liquor. For example, if there is a volume deficiency of the wash liquor such that the chips are not immersed in the wash liquor, then additional fresh water or another liquid comprising biomass hydrolysate may be added to make up the volume deficiency. If diluting the wash liquor, the other diluting liquid (e.g., fresh water) can be added before, after, or simultaneously with the addition of the wash liquor. In some embodiments, the first wash liquor comprises the wash liquor and optionally fresh water. The mixture is then heated in Step B (i.e., "heating") at a first temperature and a first pressure for a first time period, thereby forming a first liquid fraction and a first solid fraction. In Step C, at least a portion of the first liquid fraction (34) is redirected from the first solid fraction (35). This redirection typically removes the first liquid fraction (34) from vessel (31), leaving behind the first solid fraction (35) in the vessel. The first liquid fraction (34) comprises a product composition that may be comprised of $C_5$ saccharides, as described elsewhere herein. In Step D, fresh water (33) is added to vessel (31) which still contains the first solid fraction (35). In some embodiments, the first liquid fraction (34) is withdrawn from vessel (31) while simultaneously filling the vessel with fresh water (33). In some embodiments, substantially no mixing occurs between the first liquid fraction and the fresh water during the simultaneous withdrawing of the first liquid fraction and filling with the fresh water. In some embodiments, at least some mixing occurs during the simultaneous withdrawing and filling. In Step E (i.e., "washing"), the first solid fraction (35) is washed with fresh water (33). The washing typically comprises heating the first solid fraction (35) and the fresh water (33) at a second temperature and a second pressure for a second time period, thereby forming a second wash liquor and a second solid fraction. In Step F, at least a portion of the second wash liquor (37) is removed from the second solid fraction (38) and may become at least a portion of the first wash liquor (36) that is used in Step A. The second wash liquor (37) may be stored in a "wash liquor tank" (39) prior to being used in Step A to form a mixture with fresh biomass, or the second wash liquor (37) may be fed directly into the vessel during filling Step A, as desired. The second solid fraction (38) may be expelled from the vessel before repeating the processing cycle using a second fresh biomass in place of the first fresh biomass. In some embodiments, the solid fraction (38) is subjected to the processing cycle at least one more time, with or without the addition of fresh biomass.

In some embodiments, the biomass is completely immersed in the fresh water or the first wash liquor, as the case may be. In some embodiments, the biomass is at least partially (e.g., at least 50 vol. %, at least 60 vol. %, at least 70 vol. %, at least 80 vol. %, or at least 90 vol. %) immersed in the fresh water or the first wash liquor, as the case may be. In some embodiments, there are no air spaces between biomass (e.g., biomass chips) after the mixture is formed.

In some embodiments, exogenous biomass-disrupting chemicals (e.g., acids, oxidants, reductants, and the like) may be added during the inventive methods. Suitable acids, for example, sulfuric acid, sulfonic acid, phosphoric acid, phosphonic acid, nitric acid, nitrous acid, hydrochloric acid, hydrofluoric acid, hydrobromic acid, hydroiodic acid, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), amino acids, carbonic acid (e.g., formed in situ by the addition of carbon dioxide), sulfurous acid (e.g., formed in situ by the addition of sulfur dioxide), or combinations thereof. In some embodiments, exogenous acid is not used. In some embodiments, exogenous biomass-disrupting chemicals are not used.

In some embodiments, during the heating stage, the liquid phase in the vessel may be circulated as the solid biomass in the vessel remains substantially stationary. In some embodiments, during the heating stage, both the liquid phase and the solid biomass may be simultaneously circulated (e.g., mixed) within the vessel. In some embodiments, during the washing stage, the liquid phase in the vessel may be circulated as the solid biomass in the vessel remains substantially stationary. In some embodiments, during the washing stage, both the liquid phase and the solid biomass may be simultaneously circulated (e.g., mixed) within the vessel. Any suitable means of mixing known in the art may be employed, including mechanical agitation, mechanical stirring, magnetic agitation, magnetic stirring, shaking, and the like. The liquid circulation can be carried out by any suitable means known in the art. In some embodiments, the liquid may flow from one portion of the digester to another portion of the digester via a liquid circulation loop (e.g., a pipe or other means of conveyance that transports the liquid). The liquid circulation loop may be internal and/or external to the digester. In the case of an external liquid circulation loop, the liquid circulation loop may be connected to a heating device to heat the liquid after it is removed from the digester and before it is reintroduced into the digester. In the case of an internal liquid circulation loop, the liquid circulation loop may be connected to a heating device to heat the liquid after it is withdrawn from the bulk liquid and before it is reintroduced into the bulk liquid.

In some embodiments, the first wash liquor comprises a wash liquor from a previous processing cycle. "Wash liquor from a previous processing cycle," as used herein, includes wash liquor obtained from a previous cycle (including immediately previous or earlier cycles) of the method performed with the same exact vessel, and also includes wash liquor obtained from a parallel process that carries out the same method in a different but substantially similar vessel (e.g., in the situation where multiple batch reactors/vessels are operating in parallel processes to increase the capacity of a processing facility). In some embodiments, a wash liquor (i.e., a liquid comprising biomass hydrolysate) may be combined with fresh water to form the first wash liquor. In this situation, the fresh water may be combined with the liquid comprising biomass hydrolysate in any suitable order. For example, the liquid comprising biomass hydrolysate may be added to the digester first, and then fresh water subsequently added, thereby forming the first wash liquor that is used during either the "heating" step or the "washing" step of the inventive methods. Alternatively, the fresh water may be added to the digester first, and then the liquid comprising biomass hydrolysate subsequently added, thereby forming the first wash liquor. In yet another embodiment, the liquid comprising biomass hydrolysate and fresh water may be added substantially simultaneously to the digester. In yet another embodiment, the liquid comprising biomass hydrolysate and fresh water may be combined to form the first wash liquor prior to adding the first wash liquor to the digester. "Liquid comprising biomass hydrolysate" may include wash liquor from a previous processing cycle, or wash liquor from a different process, and in some embodiments fresh water may be added to the liquid comprising biomass hydrolysate to form the first wash liquor (in any suitable order, as described herein).

In some embodiments, the portion of the second wash liquor is used as at least a portion of the first wash liquor in the repeating. In some embodiments, the first wash liquor consists of the second wash liquor. In some embodiments, the first wash liquor consists of the second wash liquor and fresh water.

Some embodiments further comprise:
pressing the second solid fraction to obtain a third solid fraction and a third liquid fraction;
wherein at least a portion of the third liquid fraction is used as at least a portion of the first wash liquor in the repeating.

In some embodiments, the first liquid fraction comprises at least a portion of the second liquid fraction and at least a portion of the third liquid fraction.

Some embodiments further comprise subjecting the second solid fraction to further treatment, including, but not limited to, hydrothermal treatment, acid hydrolysis, enzymatic hydrolysis, solvent extraction, and combinations thereof. Some embodiments further comprise subjecting the third solid fraction to further treatment, including, but not limited to, hydrothermal treatment, acid hydrolysis, enzymatic hydrolysis, solvent extraction, and combinations thereof.

In some embodiments, the hydrothermal treatment comprises contacting the second solid portion with at least one fluid selected from the group consisting of supercritical fluid, near critical fluid, subcritical fluid, hot compressed water, and combinations thereof. In some embodiments, the hydrothermal treatment comprises contacting the third solid portion with at least one fluid selected from the group consisting of supercritical fluid, near critical fluid, subcritical fluid, hot compressed water, and combinations thereof.

In some embodiments, at least one of the first fresh biomass and the second fresh biomass independently is selected from the group consisting of a cellulosic material, paper, cardboard, lignocellulosic material, municipal waste, municipal solid waste, manufacturing waste, food waste, agricultural residue, corn stover, sugarcane bagasse, grass, bark, dedicated energy crops, wood residue, sawmill and paper mill discards, hardwood, softwood, plastic, synthetic polymers, synthetic oligomers, natural polymers, natural oligomers, or combinations thereof.

In some embodiments, the product composition comprises $C_5$ saccharides, including, but not limited to, sugars selected from the group consisting of $C_5$ oligosaccharides, xylose, arabinose, lyxose, ribose, rhamnose, galactose, mannose, and combinations thereof. The inventive methods may also be used to extract $C_6$ saccharides from the biomass, such as glucose and cello-oligosaccharides, though the $C_6$ saccharides typically are extracted from the biomass in a lesser amount than the amount of $C_5$ saccharides that may be extracted.

In some embodiments, at least one of the first wash liquor and the second wash liquor has a concentration of $C_5$ saccharides which is about 5 times to about 10 times, preferably about 6 times to about 9 times, less than the concentration of the $C_5$ saccharides in the product composition.

In some embodiments, a weight ratio of furfural to xylose is less than about 0.4 in the product composition. For example, a weight ratio of furfural to xylose in the product composition can be less than about 0.4, e.g., less than about 0.35, less than about 0.3, less than about 0.25, less than about 0.2, less than about 0.15, less than about 0.1, or less than about 0.05. Alternatively, or in addition, a weight ratio of furfural to xylose in the product composition can be at least about 0.01, e.g., at least about 0.05, at least about 0.1, at least about 0.15, at least about 0.2, at least about 0.25, at least about 0.3, or at least about 0.35. Thus, the weight ratio of furfural to xylose in the product composition can be bounded by any two of the foregoing endpoints. For example, the weight ratio of furfural to xylose in the product composition can be about 0.05 to about 0.2, about 0.35 to about 0.4, or about 0.01 to about 0.3.

In some embodiments, the yield of xylose (as xylose monomer or as xylose monomer in combination with xylo-oligosaccharides expressed in xylose equivalent) is about 40% to about 100% of the theoretical yield of xylose. Although 100% xylose yield is theoretically possible, at least some portion of xylose typically converts to one or more byproducts, such as furfural, during biomass treatment processes, and thus it is difficult to obtain 100% xylose yield. The xylose yield can be about 40% or more, e.g., about 45% or more, about 50% or more, about 55% or more, about 60% or more, about 65% or more, about 70% or more, about 75% or more, about 80% or more, about 85% or more, about 90% or more, about 95% or more, or about 100%. The yields disclosed hereinabove may also be applicable to other $C_5$ saccharides (such as arabinose, lyxose, ribose, xylulose, or combinations thereof) or $C_6$ saccharides (such as glucose, mannose, galactose and/or cello-oligosaccharides). Similar to the yields of $C_5$ saccharides, the yields of $C_6$ saccharides can be expressed as monomer or as monomer equivalent.

In some embodiments, the percent conversion of a given polysaccharide is about 30% to about 100%. The percent conversion is calculated by subtracting the amount of a specific polysaccharide (e.g., glucan or xylan) remaining after performing the method from the amount of the specific polysaccharide (e.g., glucan or xylan) in the starting composition, and dividing the result by the amount of the specific polysaccharide (e.g., glucan or xylan) in the starting composition. The percent conversion can be about 30% or more, e.g., about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%.

In some embodiments, the first temperature is about 110° C. to about 220° C. For example, the first temperature is at least about 110° C., e.g., at least about 120° C., at least about 130° C., at least about 140° C., at least about 150° C., at least about 160° C., at least about 170° C., at least about 180° C., at least about 190° C., at least about 200° C., or at least about 210° C. Alternatively, or in addition, the first temperature is less than about 220° C., e.g., less than about 210° C., less than about 200° C., less than about 190° C., less than about 180° C., less than about 170° C., less than about 160° C., less than about 150° C., less than about 140° C., less than about 130° C., or less than about 120° C. Thus, the first temperature can be bounded by any two of the foregoing endpoints. For example, the first temperature can be about 120° C. to about 180° C., about 140° C. to about 210° C., or about 190° C. to about 220° C. In a preferred embodiment, the first temperature is about 130° C. to about 190° C.

In some embodiments, the second temperature is about 80° C. to about 190° C. For example, the second temperature is at least about 80° C., e.g., at least about 90° C., at least about 100° C., at least about 110° C., at least about 120° C., at least about 130° C., at least about 140° C., at least about 150° C., at least about 160° C., at least about 170° C., or at least about 180° C. Alternatively, or in addition, the second temperature is less than about 190° C., e.g., less than about 180° C., less than about 170° C., less than about 160° C., less than about 150° C., less than about 140° C., less than about 130° C., less than about 120° C., less than about 110° C., less than about 100° C., or less than about 90° C. Thus, the second temperature can be bounded by any two of the foregoing endpoints. For example, the second temperature can be about 110° C. to about 170° C., about 130° C. to about 190° C., or about 90° C. to about 120° C. In a preferred embodiment, the second temperature is about 140° C. to about 170° C., more preferably about 145° C. to about 165° C.

In some embodiments, the second temperature is less than the first temperature. Without wishing to be bound by theory, it is thought that keeping the second temperature lower than the first temperature may help to minimize the production of undesirable degradation products, such as furfural and formic acid, for example, during the washing.

In some embodiments, the first time period is about 10 min to about 140 min. For example, the first time period is at least about 10 min, e.g., at least about 20 min, at least about 30 min, at least about 40 min, at least about 50 min, at least about 60 min, at least about 70 min, at least about 80 min, at least about 90 min, at least about 100 min, at least about 110 min, at least about 120 min, or at least about 130 min. Alternatively, or in addition, the first time period is less than about 140 min, e.g., less than about 130 min, less than about 120 min, less than about 110 min, less than about 100 min, less than about 90 min, less than about 80 min, less than about 70 min, less than about 60 min, less than about 50 min, less than about 40 min, less than about 30 min, or less than about 20 min. Thus, the first time period can be bounded by any two of the foregoing endpoints. For example, the first time period can be about 30 min to about 80 min, about 20 min to about 50 min, or about 80 min to about 100 min. In a preferred embodiment, the first time period is about 70 min to about 110 min.

In some embodiments, the second time period is about 20 min to about 120 min. For example, the second time period is at least about 20 min, e.g., at least about 30 min, at least about 40 min, at least about 50 min, at least about 60 min, at least about 70 min, at least about 80 min, at least about 90 min, at least about 100 min, or at least about 110 min. Alternatively, or in addition, the second time period is less than about 120 min, e.g., less than about 110 min, less than about 100 min, less than about 90 min, less than about 80 min, less than about 70 min, less than about 60 min, less than about 50 min, less than about 40 min, or less than about 30 min. Thus, the second time period can be bounded by any two of the foregoing endpoints. For example, the second time period can be about 30 min to about 100 min, about 70 min to about 110 min, or about 40 min to about 120 min. In a preferred embodiment, the second time period is about 20 min to about 70 min.

In some embodiments, the processing cycle (i.e., a single processing cycle without the repeating) has a total duration of about 30 min to about 300 min. For example, the processing cycle has a total duration of at least about 30 min, e.g., at least about 40 min, at least about 50 min, at least about 60 min, at least about 70 min, at least about 80 min, at least about 90 min, at least about 100 min, at least about 110 min, at least about 120 min, at least about 130 min, at least about 140 min, at least about 150 min, at least about 160 min, at least about 170 min, at least about 180 min, at least about 190 min, at least about 200 min, at least about 210 min, at least about 220 min, at least about 230 min, at least about 240 min, at least about 250 min, at least about 260 min, at least about 270 min, at least about 280 min, or at least about 290 min. Alternatively, or in addition, the processing cycle has a total duration of less than about 300 min, e.g., less than about 290 min, less than about 280 min, less than about 270 min, less than about 260 min, less than about 250 min, less than about 240 min, less than about 230 min, less than about 220 min, less than about 210 min, less than about 200 min, less than about 190 min, less than about 180 min, less than about 170 min, less than about 160 min, less than about 150 min, less than about 140 min, less than about 130 min, less than about 120 min, less than about 110 min, less than about 100 min, less than about 90 min, less than about 80 min, less than about 70 min, less than about 60 min, less than about 50 min, less than about 40 min, or less than about 30 min. Thus, the processing cycle can have a total duration bounded by any two of the foregoing endpoints. For example, the processing cycle can have a total duration of about 30 min to about 120 min, about 100 min to about 220 min, or about 200 min to about 260 min. In a preferred embodiment, the processing cycle has a total duration of about 190 min to about 220 min.

In some embodiments, the first pressure is sufficient to maintain any water present in substantially liquid form. In some embodiments, the first pressure is higher than atmospheric pressure. In some embodiments, the first pressure is higher than a pressure sufficient to maintain any water present in substantially liquid form.

In some embodiments, the second pressure is sufficient to maintain any water present in substantially liquid form. In some embodiments, the second pressure is higher than atmospheric pressure. In some embodiments, the second pressure is atmospheric pressure. In some embodiments, the second pressure is higher than a pressure sufficient to maintain any water present in substantially liquid form.

In some embodiments, the processing cycle produces a product composition with an increased level of $C_5$ saccharides relative to a batch processing cycle without the redirecting, washing, removing, and repeating steps.

In some embodiments, a weight ratio of water added during the heating and/or washing steps to the dry biomass is about 10 to about 1. The weight ratio referred to in this paragraph is relative to the amount of biomass added in one cycle of the method (and does not include additional biomass added during a repeating step). For example, a weight ratio of water added during the heating and/or washing steps to the dry biomass is less than about 10, e.g., less than about 9.5, less than about 9, less than about 8.5, less than about 8, less than about 7.5, less than about 7, less than about 6.5, less than about 6, less than about 5.5, less than about 5, less than about 4.5, less than about 4, less than about 3.5, less than about 3, less than about 2.5, less than about 2, less than about 1.5, or less than about 1. Alternatively, or in addition, a weight ratio of water added during the heating and/or washing steps to the dry biomass is at least about 1, e.g., at least about 1.5, at least about 2, at least about 2.5, at least about 3, at least about 3.5, at least about 4, at least about 4.5, at least about 5, at least about 5.5, at least about 6, at least about 6.5, at least about 7, at least about 7.5, at least about 8, at least about 8.5, at least about 9, at least about 9.5, or at least about 10. Thus, the weight ratio can be bounded by any two of the foregoing endpoints. For example, the weight ratio can be about 2 to about 4, about 6 to about 8.5, or about 3 to about 3.5. In a preferred embodiment, the weight ratio is about 2 to about 4, more preferably about 2.5 to about 3.5.

In some embodiments, a weight ratio of total water added during the method to dry biomass is about 10 to about 1. The weight ratio referred to in this paragraph is relative to the amount of biomass added in one cycle of the method (and does not include additional biomass added during a repeating step). For example, a weight ratio of total water added during the method to dry biomass is less than about 10, e.g., less than about 9.5, less than about 9, less than about 8.5, less than about 8, less than about 7.5, less than about 7, less than about 6.5, less than about 6, less than about 5.5, less than about 5, less than about 4.5, less than about 4, less than about 3.5, less than about 3, less than about 2.5, less than about 2, less than about 1.5, or less than about 1. Alternatively, or in addition, a weight ratio of total water added during the method to dry biomass is at least about 1, e.g., at least about 1.5, at least about 2, at least about 2.5, at least about 3, at least about 3.5, at least about 4, at least about 4.5, at least about 5, at least about 5.5, at least about 6, at least about 6.5, at least about 7, at least about 7.5, at least about 8, at least about 8.5, at least about 9, at least about 9.5, or at least about 10. Thus, the weight ratio can be bounded by any two of the foregoing endpoints. For example, the weight ratio can be about 2.5 to about 6, about 7.5 to about 10, or about 3.5 to about 4. In a preferred embodiment, the weight ratio is about 4 to about 6, more preferably about 4.5 to about 5.5.

In some embodiments, at least one of the first fresh biomass and the second fresh biomass is subjected to steaming, prior to the forming.

In further embodiments, the invention is directed to a system, comprising:
 a batch digester, comprising:
  a first end;
  a second end;
  a heating device;
  a wash liquor tank in fluid communication with the first end of the batch digester;
  a product tank in fluid communication with the second end of the batch digester; and
  a press in fluid communication with the second end of the batch digester.

The system can be used to carry out the inventive methods disclosed herein. A representative system is shown in FIG. 1. The system (18) typically comprises a batch digester (11) comprising a first end (12), a second end (13), a heating device (14), a wash liquor tank (15) in fluid communication with the first end (12) of the batch digester (11), a product tank (16) in fluid communication with the second end (13) of the batch digester (11), and a press (17) in fluid communication with the second end (13) of the batch digester (11). In FIG. 1, the heating device is shown as an external heating element, but any suitable heating device may be employed, as described herein.

In some embodiments, the heating device is selected from the group consisting of an external heating device, an external heat exchanger, a steam injector, and combinations thereof.

In some embodiments, the system comprises a fluid circulation loop. For example, fluid may flow from one portion of the digester to another portion of the digester via a fluid circulation loop (e.g., a pipe or other means of conveyance that transports the fluid). The fluid circulation loop may be internal and/or external to the digester. In some embodiments, the fluid circulation loop is connected to the heating device to heat the liquid after it is removed from the digester and before it is reintroduced into the digester.

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Comparative Example 1

Figure 4:
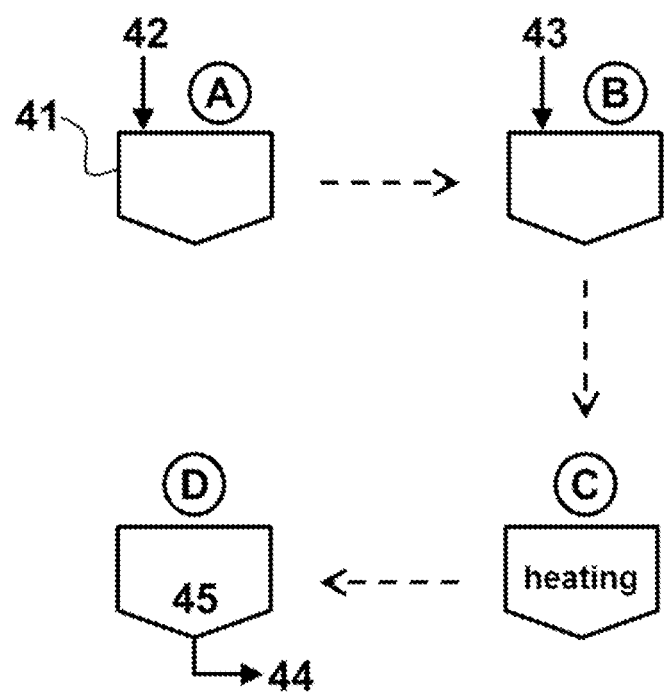
FIG. 4 is a schematic diagram showing a comparative method.

FIG. 4 depicts a conventional batch digestion without a wash cycle. In Step A, 709.5 kg of woody biomass (e.g., wood chips, 40% moisture content) (not shown) present in vessel (41) is first steamed (42) to displace the air contained in them for 15 minutes. This procedure is sometimes employed in the pulp and paper industry, especially when a catalyst is used in a subsequent step. In Step B, 1229 kg of hot water (43) at a slightly lower temperature than the steam temperature is added to the vessel. With the addition of this cooler water, steam trapped in the interstices/pores of the wood chips condenses, creating a vacuum that helps the water or water/catalyst mixture to penetrate into the pores. In this particular example, water is circulated for 75 minutes in Step C, while rapidly bringing the temperature up to a reaction temperature of about 165° C. In Step D, the liquid (44) containing sugars (derived from hemicellulose) and by-products (such as furfural and acetic acid) is first discharged to a tank, and then the solids (45) are blown to a blow tank (not shown) for further processing.

Figure 9:
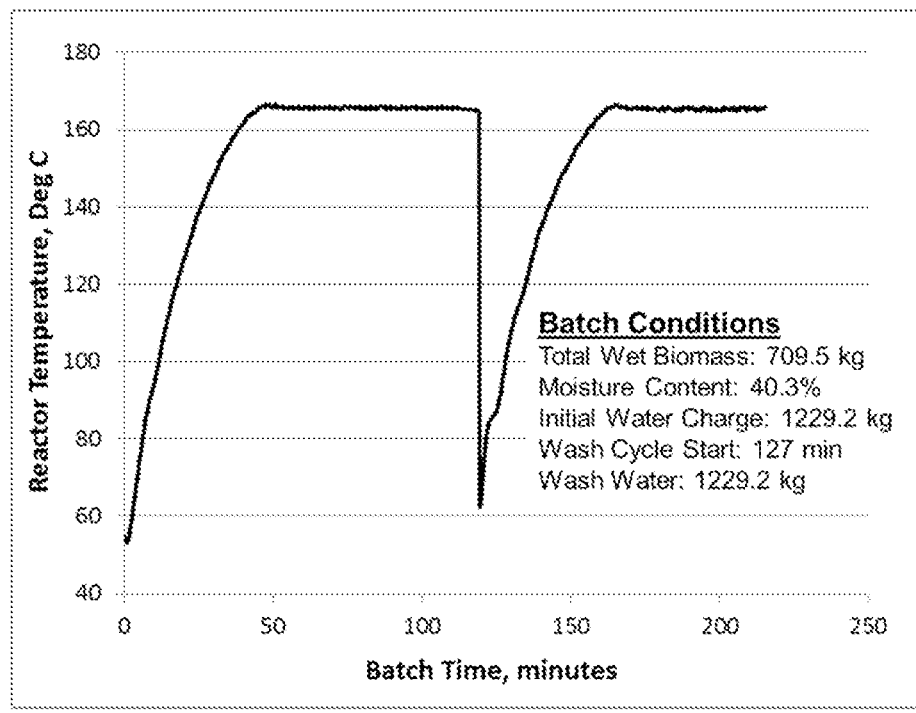
FIG. 9 is a plot of reaction temperature as a function of time for a comparative method.

The composition of the polysaccharides contained in the added woody biomass, on a water-free basis, is shown in Table 1. Further details on process conditions, such as the temperature profile over time, are shown in FIG. 9 (up until about 127 min, since there is no wash cycle in this comparative example).

TABLE 1

| Component | Weight % |
|---|---|
| Xylan | 18.84 |
| Glucan | 40.62 |
| Acetate | 4.18 |
| Arabinan | 0.87 |
| Ash | 0.47 |
| Lignin | 27.31 |
| Unknowns | 7.72 |

Figure 5:
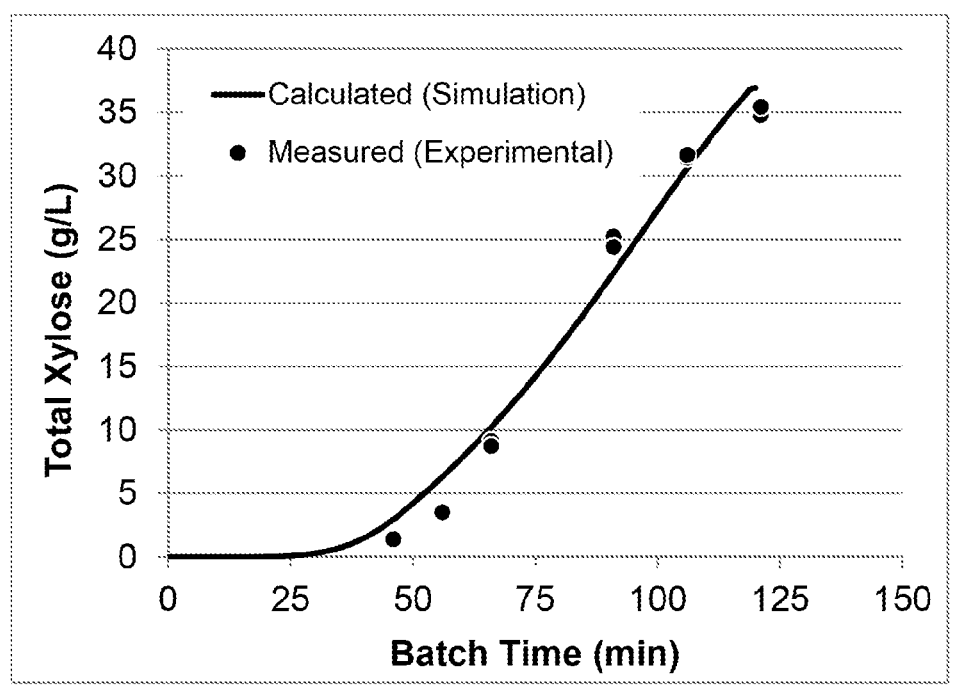
FIG. 5 is a plot of total xylose concentration as a function of time for a comparative example.

In this process, xylan contained in the biomass is converted to xylose and xylo-oligosaccharides (the sum of which is the "total xylose"). FIG. 5 shows the total xylose concentration as a function of time resulting from the process of FIG. 4. As shown in FIG. 5, the total xylose concentration reaches about 35 g/liter in about 120 minutes. In FIG. 5, the circles are the measured experimental data, and the solid line is the numerical simulation of the reaction progress using a kinetic model and a reactor model, the reaction conditions, and the initial starting compositions. The model tracks the trends and the final outcome well. The calculated (from simulations) and measured total xylose yields (as defined herein) are 40.6% and 42.5%, respectively. The calculated (from simulations) and measured xylan conversions for this experiment are 65.8% and 58%, respectively.

Figure 6:
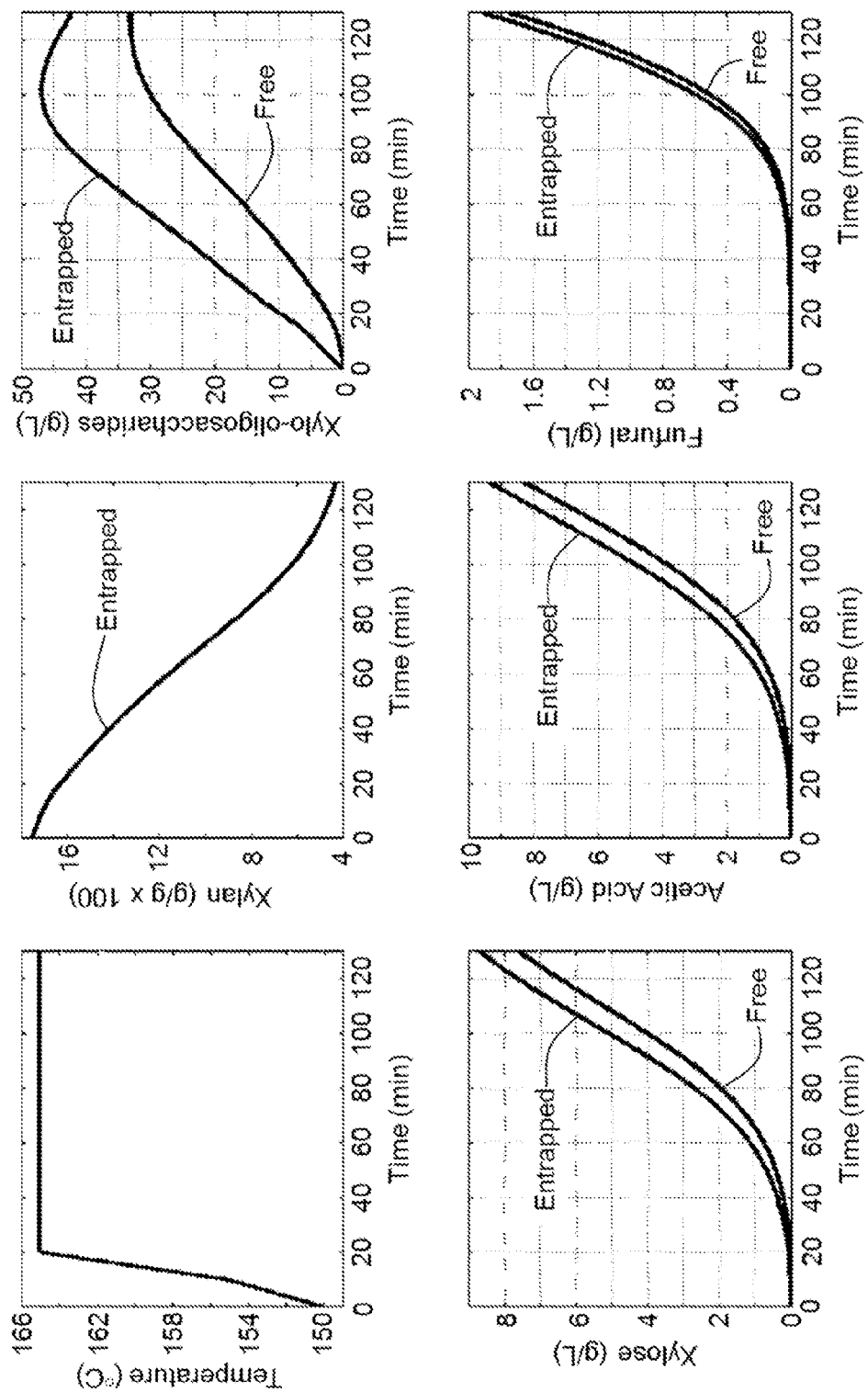
FIG. 6 shows plots of temperature, xylan, xylo-oligosaccharides, xylose, acetic acid, and furfural as a function of time for a comparative example.

FIG. 6 shows the results of a simulation of a similar experiment, except the temperature/time profile is different. FIG. 6 depicts the heating profile used for this simulation, as well as the concentration of acetic acid and furfural, which are reaction by-products. The batch reactor is charged with wood chips, and the water-to-chips (bone dry basis) ratio is kept around 2.9 (in a batch system, typically it is difficult to reduce this ratio much less than this value if the chips are to be held totally immersed). The amount of reactor charge is the same as in the experiment and simulation that generated the results of FIG. 5 (see batch conditions shown in FIG. 9). The initial xylan fraction for the simulation of FIG. 6 is 0.175.

FIG. 6 shows the concentration of sugars (xylose and xylo-oligosaccharides) that is (a) in the pores of the wood chips ("Entrapped") and (b) in the bulk liquor ("Free"). As shown, significant amounts of xylo-oligosaccharides and xylose monomer are left behind within the wood chip. In continuous vertical digesters, different methods can be employed in an attempt to recover the sugars that are left behind. For example, the chips can be subjected to a counter-current wash in the "wash" zone as described above. In this zone, the sugars and by-products are allowed to diffuse out into the bulk liquor. The wash zone can be designed to remove close to 100% of the remaining sugars and by-products. Another option to remove the sugars is to use a press to "squeeze" out the sugars. Single stage pressing is not very effective, since about 35-50% of the sugars remain in the chip, depending on the available pore volume and trapped free water in the chip. The pressing efficiency can be increased by additional presses at the expense of extra time and capital. Even then, however, reaching a 100% recovery of the remaining xylose and xylo-oligosaccharides is difficult to attain.

The total xylose yields attained in this experiment is about 48.2% and the xylan conversion is about 75.3%. Even though this yield can be slightly improved by manipulating the time and temperature, it cannot reach the levels attained using a vertical digester or using a series of presses to recover the entrapped sugars. In a conventional batch digester, wood chips typically are stationary, and the liquor typically is circulated. In the conventional operation of a batch digester, it is not possible to carry out the conversion and washing stages as efficiently as when a continuous digester is employed.

Comparative Example 2

This example demonstrates the benefits of performing a washing cycle, a pressing cycle, or both, in a digestion process for hydrolyzing biomass.

One way to increase the total xylose yield in a batch reaction is to carry out a wash after the concentration of xylose oligomers reaches a maximum in the digester. In FIG. 6, which depicts data obtained from the heating of biomass in fresh water without a wash cycle, the maximum xylose oligomer concentration in the liquor (i.e., "Free" xylo-oligosaccharides) is achieved after approximately 130 minutes. At this point, the liquor in the digester can be emptied and fresh water charged and circulated for a given amount of time to wash the "cooked" biomass. During this time, the sugars and by-products contained within the pores are allowed to diffuse into the bulk liquor. This wash step is a continuation of Step D from FIG. 4. After the wash cycle, the chips can be "blown" out of the vessel by pressurizing the vessel with steam, and then opening a valve leading to a collection tank, thereby causing the hydrolyzed chips to "blow" into the collection tank.

Figure 8:
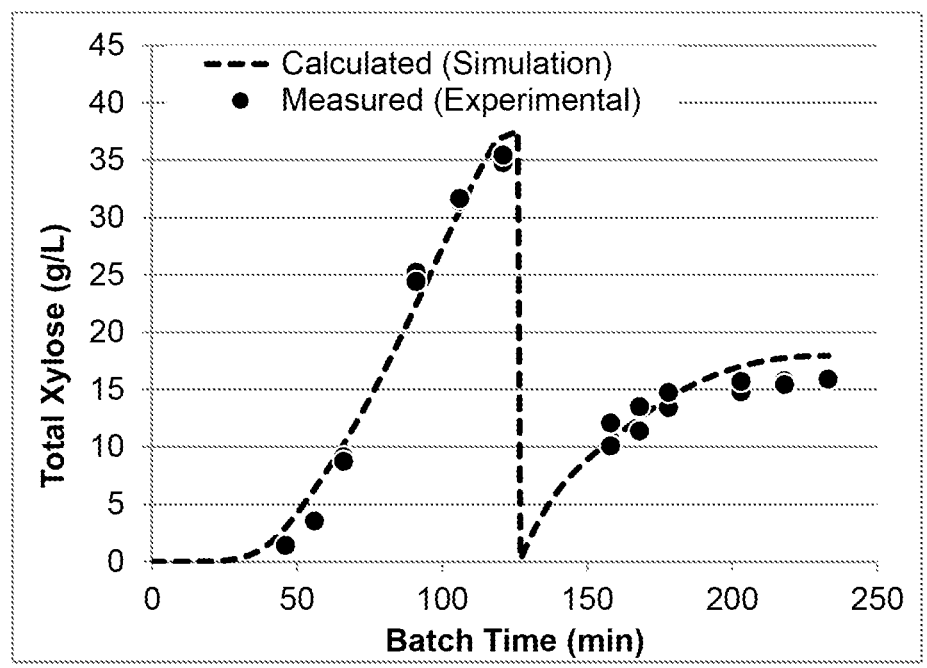
FIG. 8 is a plot of simulated data and experimental data of total xylose concentration as a function of time for a comparative method.

There are two examples showing the benefits of a wash cycle. The first example is a theoretical prediction, and the second example shows actual data together with the theoretical prediction. As depicted in FIG. 8, which is discussed in more detail hereinbelow, the theoretical prediction of the end point is within about 95% of the experimental data.

Figure 7:
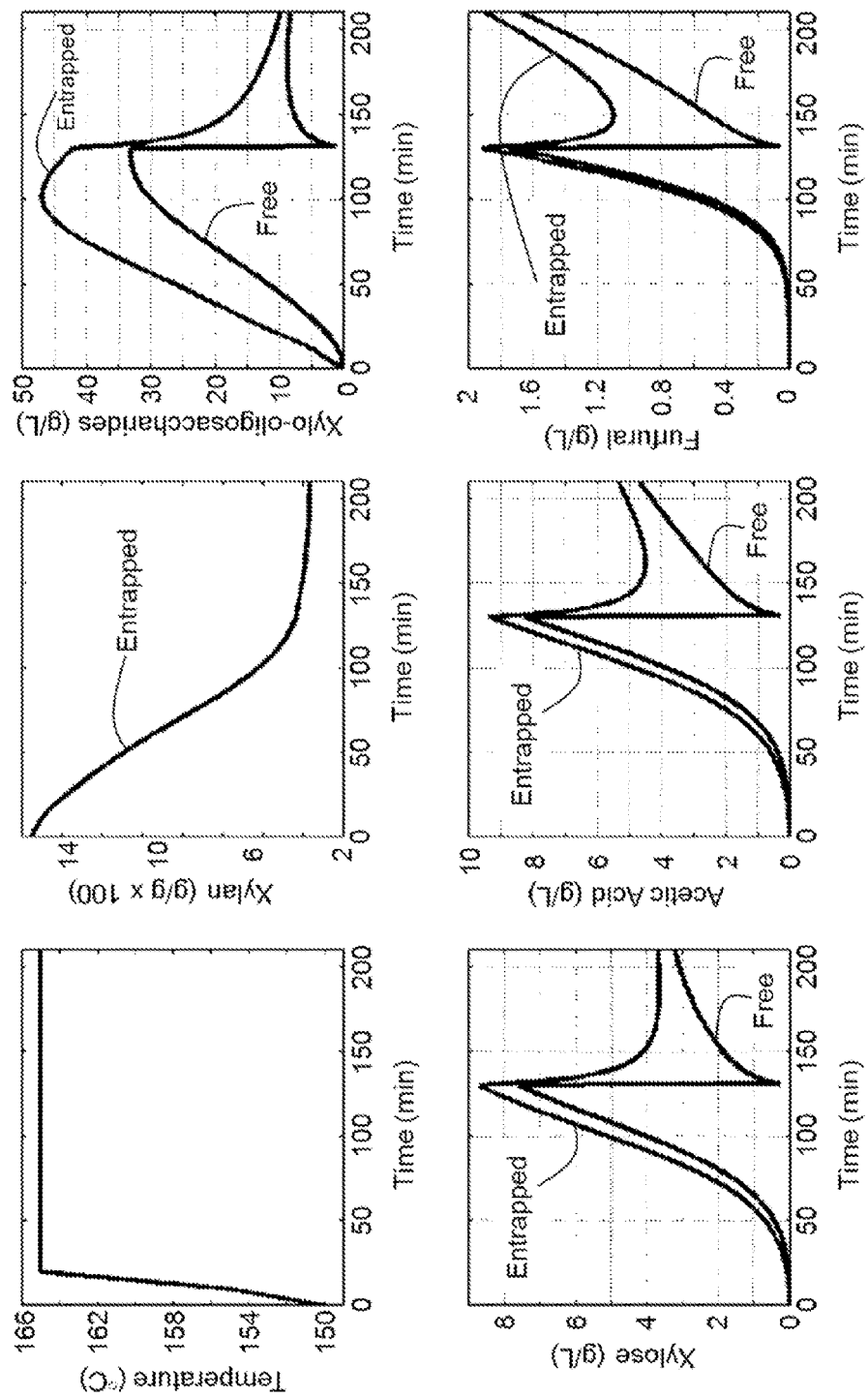
FIG. 7 shows plots of temperature, xylan xylo-oligosaccharides, xylose, acetic acid, and furfural as a function of time for a comparative method.

FIG. 7 shows the theoretical results obtained from adding a 75 minute wash cycle to the simulation shown in FIG. 6. The wash cycle increases the total xylose yield to about 64.8% and the xylan conversion to about 79.2% at the expense of diluting the sugars, since additional water equal to the amount of the initial water charge is added to the batch reactor in the wash cycle, bringing the overall liquid-to-solids ratio (bone dry basis) to nearly six (2.9×2). The total xylose yield can be further increased by a percentage point or two through some optimization of the process, but it is difficult to exceed a yield of about 70%. In these simulations, water is introduced at about 130 minutes. The heating profile for the simulation is shown in the top left graph of FIG. 7.

FIG. 8 shows experimental (circles) and calculated (dashed line) results obtained from adding a 75 minute wash cycle (circulating the wash liquor at 165° C.) to the experiment shown in FIG. 5. Table 2 contains the experimental results in tabular form. The wash cycle is accomplished by first emptying the vessel at about the 130 min mark (i.e., after about 75 min at about 165° C.), filling the vessel with fresh water, re-heating it to a wash temperature of 165° C., and holding it at this temperature for 75 minutes. FIG. 9 shows the temperature profile over time for the data shown in FIG. 8 and Table 2.

The total xylose yield for the entire run, including the wash cycle, is about 62% (experimental), whereas the predicted yield from the simulation is about 65.8%. The inclusion of the wash cycle increases the yield from about 42.46% to about 62.43% for experimental results and from about 40.6% to about 65.8% for the simulations.

TABLE 2

| Time (minutes) | Total Xylose (g/L) | Furfural (g/L) | Acetic Acid (g/L) |
| --- | --- | --- | --- |
| 46.00 | 1.35 | 0.00 | 0.73 |
| 46.00 | 1.42 | 0.06 | 0.75 |
| 56.00 | 3.48 | 0.05 | 0.87 |
| 56.00 | 3.54 | 0.02 | 0.85 |
| 66.00 | 9.14 | 0.02 | 1.47 |
| 66.00 | 8.74 | 0.06 | 1.40 |
| 91.00 | 25.23 | 0.24 | 2.83 |
| 91.00 | 24.42 | 0.23 | 2.54 |
| 106.00 | 31.41 | 0.40 | 3.77 |
| 106.00 | 31.66 | 0.47 | 3.54 |
| 121.00 | 34.77 | 0.88 | 4.69 |
| 121.00 | 35.44 | 0.79 | 4.22 |
| 158.00 | 10.08 | 0.32 | 1.79 |
| 158.00 | 12.08 | 0.29 | 1.80 |
| 168.00 | 11.39 | 0.30 | 2.00 |
| 168.00 | 13.51 | 0.36 | 1.89 |
| 178.00 | 13.42 | 0.37 | 2.22 |
| 178.00 | 14.74 | 0.36 | 2.15 |
| 203.00 | 14.80 | 0.50 | 2.59 |
| 203.00 | 15.70 | 0.49 | 2.37 |
| 218.00 | 15.78 | 0.73 | 3.10 |
| 218.00 | 15.44 | 0.69 | 2.67 |
| 233.00 | 15.89 | 0.87 | 3.49 |

Another possible way to increase the yield is to press the chips after Step D of FIG. 4. As mentioned above, pressing recovers about 50% of the remaining sugar in the wood chip, which slightly increases the yield, assuming that in the wood chip about half of the volume of the water is bound and the other half is free water in the pores, which is consistent with literature observations. As used herein, "free water" is the water than can be pressed from the biomass chips and is not adsorbed to the surfaces of the chips. In contrast, "bound water" is water that is adsorbed to the surfaces of the chips and cannot be removed by mere pressing.

Table 3 shows the starting biomass chip mass, biomass chip moisture content, water charge, and amount of xylan contained in the biomass chips for the simulations of FIGS. 8 and 9. Table 3 also shows, starting with these given inputs, the results of performing (1) digestion only (i.e., without washing or pressing) (2) with pressing but not washing, (3) with washing but not pressing, and (4) with both washing and pressing.

TABLE 3

| Input | |
| --- | --- |
| Wet chip charge, kg | 709.5 |
| Chip moisture, % | 40% |
| Water added, kg | 1229.2 |
| Xylan incoming with chips (solids), kg | 74.1 |
| Xylose equivalent in chips, kg | 84.2 |
| Digest Only | |
| Xylan out, kg | 18.3 |
| Xylan conversion, % | 75.3 |
| Entrapped water in pores (free + bound), kg | 514 |
| Xylose equivalent contained in liquor, kg | 40.6 |
| Yield, % (digest only) | 48.2 |
| Digest + Press | |
| Xylose equivalent contained in solids, kg | 11.7 |
| Recovered xylose equivalent from pressing (assuming all free liquor in chip is removed by pressing), kg | 5.85 |
| Total xylose recovered, kg | 46.4 |
| Yield, % (digest + press) | 55.1 |
| Digest + Wash | |
| Xylose equivalent contained in solids after wash, kg | 6.91 |
| Xylose in liquor after wash, kg | 54.7 |
| Yield, % (digest + wash) | 64.8 |
| Digest + Wash + Press | |
| Xylose equivalent recovered by pressing after wash, kg | 3.46 |
| Total xylose equivalent recovery in wash + press, kg | 58.2 |
| Yield, % (digest + wash + press) | 69 |

As shown in Table 3, the yield of total xylose with digestion only (i.e., without the pressing or washing steps) is 48.2% and the yield after digestion and pressing (i.e., without washing) is 55.1%. However, pressing does not achieve as high a yield as when the solids are washed after digestion, resulting in a yield of 64.8% (i.e., for digestion and washing, but no pressing). Also shown in Table 3 is the total xylose yield (69%) achieved from the combination of digestion, washing, and then pressing, which achieves the best overall yield of the different comparative methods to recover the most amount of total xylose.

Example 1

In this example, it is demonstrated that, at a given total liquor-to-chip ratio, a batch sequencing process according to the invention can achieve yields and conversions that are similar to, and typically higher than, those achieved using continuous vertical digesters. One advantage of using a method according to the invention is that batch reactors are much simpler and cheaper to construct compared to continuous vertical digesters.

An apparatus that may be used for the batch sequence steps of a method of the invention is shown in FIG. 1.

Employing a method of the invention, which comprises a sequence of liquor removal and recycling/washing steps, provides a total xylose yield that typically is higher than the total xylose yield obtained from the batch hydrolysis of biomass demonstrated in Comparative Example 2. Besides increased yield (and conversion), another advantage of the invention is to minimize the liquor-to-solid ratio (bone dry basis, wt./wt.), which, for this example, is maintained at about five to one. This liquor-to-solid ratio can be achieved by employing the batch sequence steps shown in FIG. 2, which is described more generally elsewhere herein. The steps set forth below are specific to this example, but generally track the steps shown in FIG. 2.

Step A: The digester (21) is charged with biomass (22) (e.g., wood chips). The wood chips are then steamed for a given period of time, preferably about 15-30 minutes at atmospheric pressure. Although this example employs steaming of the chips, the steaming is not required, but may be performed to improve infiltration of water into the pores of the wood chips upon the addition of water. After the steaming is finished, the digester is filled with water (23) at a slightly lower temperature than the steam temperature.

Step B: The liquor is circulated in the digester and rapidly heated through an external heater or by steam injection. The wood chips are then "cooked" (i.e., heated) for a given amount of time, preferably 15 minutes to 100 minutes at a temperature ranging from about 130° C. to about 190° C. During this step, the xylan contained in the wood chips undergoes autohydrolysis.

Steps C and D: The "cooked liquor" (24) (containing biomass hydrolysate) is removed from the digester, either before the "wash liquor" (26) is added, or simultaneously during the addition of the "wash liquor" (26). In this example, Steps C and D are performed simultaneously. Furthermore, it is assumed in this example that the liquor coming from the wash liquor tank is about at the same temperature as the liquor in the digester, and that the withdrawing liquor moves down the digester with little back mixing with the added wash liquor. The "wash liquor" is a recycled dilute sugar (e.g., xylose) solution, which is collected in Step F. The "cooked" solids (25) are left behind in the digester to be washed in a subsequent step. While Steps C and D are being performed, the temperature of the liquor in the batch reactor is reduced (gradually, or more preferably rapidly) to slow down and minimize the sugar degradation reactions. After the wash liquor is depleted, fresh water is introduced into the digester to make up a volume deficiency in the digester while still simultaneously withdrawing the hydrolysate (e.g., the volume of wash liquor may be insufficient to fully displace the hydrolysate from Step C). In some cases it is particularly desirable to add this extra fresh water, so as to dilute the wash liquor and improve the amount of sugars extracted in the subsequent washing step (and possibly to also further minimize degradation reactions).

Step E: Once the right amount of the water is charged to the reactor, the liquor is circulated for a time period for the wash cycle. At the end of the wash cycle, the resulting wash liquor is collected in a wash liquor tank. The wash liquor is a dilute solution of sugars (e.g., comprising xylose and xylo-oligosaccharides).

Figure 10:
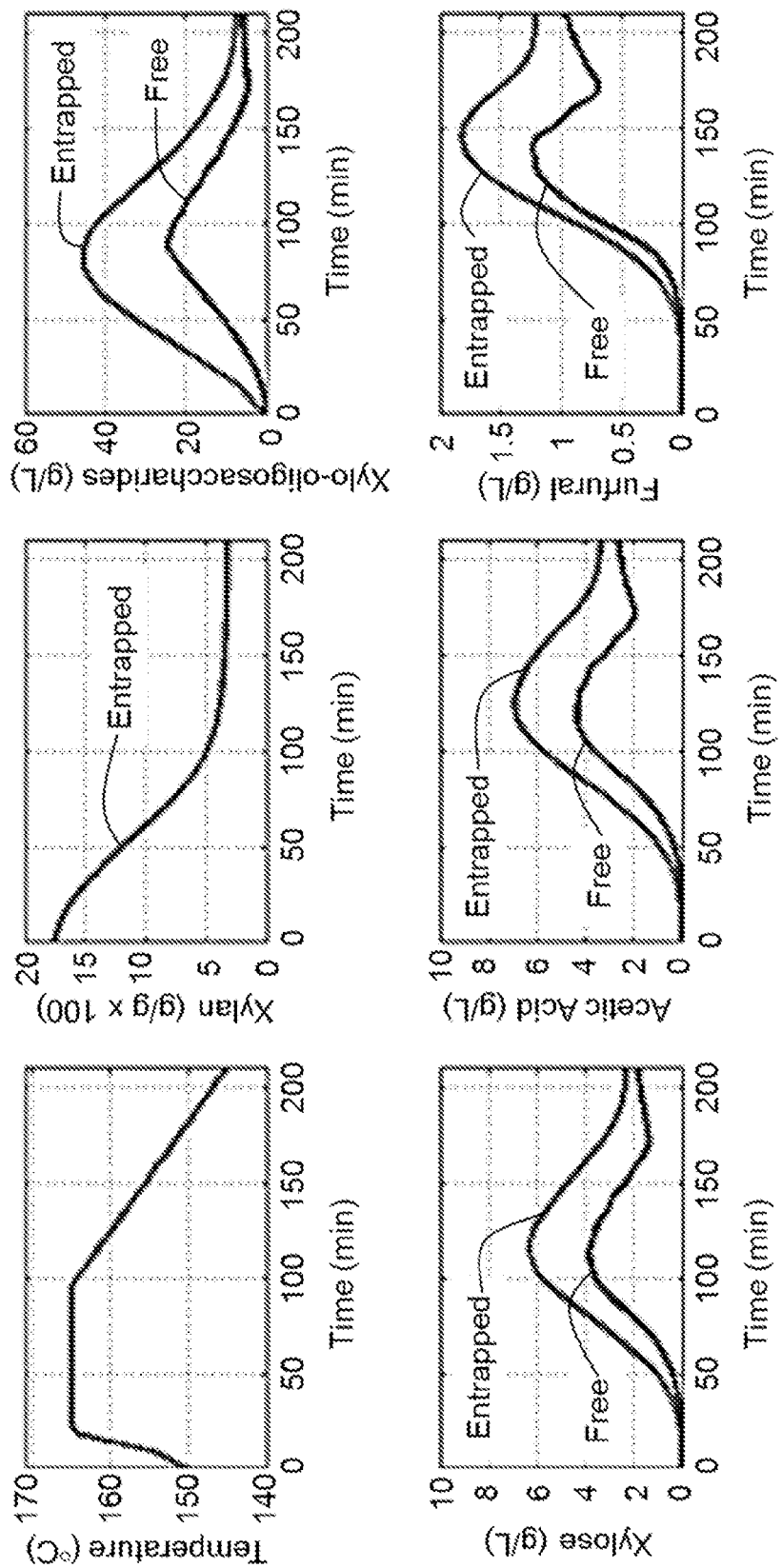
FIG. 10 shows plots of temperature, xylan, xylo-oligosaccharides, xylose, acetic acid, and furfural as a function of time for an embodiment of the invention.

FIG. 10 shows the results of a simulation according to this example. In this particular example, about 53.9 tons of wood chips and about 146 tons of water are charged into the digester. Moreover, the following time periods were employed:

Step B (batch cook time)=90 minutes
Steps C & D (liquor discharge and simultaneous wash liquor addition, except addition of fresh water)=45 minutes
Addition of fresh water in Step D=35 minutes
Step E (batch wash time)=40 minutes
Total active reactor time=210 minutes.

In this example, a total xylose yield of 72.7% and a xylan conversion of 81.8% are achieved, both of which are higher than the yields or conversions in any of the comparative examples.

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as temperature ranges and pressure ranges, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for biomass hydrolysis to maximize sugar yields from the biomass comprising, in a processing cycle:
   forming a mixture comprising fresh water and a first fresh biomass;
   heating the mixture at a first temperature and a first pressure for a first time period, thereby forming a first liquid fraction and a first solid fraction
   redirecting at least a portion of the first liquid fraction from the first solid fraction,
      wherein the first liquid fraction comprises a product composition;
   washing the first solid fraction with a first wash liquor;
      optionally, wherein the first wash liquor comprises a wash liquor from a previous processing cycle;
      wherein the washing comprises heating the first solid fraction and the first wash liquor at a second temperature and a second pressure for a second time period, thereby forming a second wash liquor and a second solid fraction;
   removing at least a portion of the second wash liquor from the second solid fraction; wherein at least a portion of one or more wash liquors is collected; wherein the first temperature is at least about 110° C. and the second temperature is less than the first temperature; and
   repeating the processing cycle using a second fresh biomass in place of the first fresh biomass;
   wherein the method is directed toward maximizing sugar yields.

2. The method of claim 1,
   wherein the portion of the second wash liquor is used as at least a portion of the first wash liquor in the repeating step.

3. The method of claim 1,
   wherein the first wash liquor comprises a wash liquor from a previous processing cycle.

4. The method of claim 1,
   wherein liquid comprising biomass hydrolysate is combined with fresh water to form the first wash liquor.

5. The method of claim 1, further comprising:
   pressing the second solid fraction to obtain a third solid fraction and a third liquid fraction,
   wherein at least a portion of the third liquid fraction is used as at least a portion of the first wash liquor in the repeating step.

6. The method of claim 1, further comprising:
   subjecting the second solid fraction to further treatment selected from the group consisting of hydrothermal treatment, acid hydrolysis, enzymatic hydrolysis, solvent extraction, and combinations thereof.

7. The method of claim 6,
   wherein the further treatment comprises hydrothermal treatment, and the hydrothermal treatment comprises contacting the second solid portion with at least one fluid selected from the group consisting of supercritical fluid, near critical fluid, subcritical fluid, hot compressed water, and combinations thereof.

8. The method of claim 1,
   wherein at least one of the first fresh biomass and the second fresh biomass independently is selected from the group consisting of a cellulosic material, paper, cardboard, lignocellulosic material, municipal waste, municipal solid waste, manufacturing waste, food waste, agricultural residue, corn stover, sugarcane bagasse, grass, bark, dedicated energy crops, wood residue, sawmill and paper mill discards, hardwood, softwood, plastic, synthetic polymers, synthetic oligomers, natural polymers, natural oligomers, and combinations thereof.

9. The method of claim 1, wherein the product composition comprises $C_5$ saccharides selected from the group consisting of $C_5$ oligosaccharides, xylose, arabinose, lyxose, ribose, and combinations thereof.

10. The method of claim 9, wherein at least one of the first wash liquor and the second wash liquor has a concentration of $C_5$ saccharides which is about 5 times to about 10 times less than the concentration of the $C_5$ saccharides in the product composition.

11. The method of claim 1, wherein, in the product composition, a weight ratio of furfural to xylose is less than 0.4.

12. The method of claim 1, wherein the first temperature is about 110° C. to about 220° C.

13. The method of claim 1, wherein the second temperature is about 80° C. to about 190° C.

14. The method of claim 1, wherein the first time period is about 10 min to about 140 min.

15. The method of claim 1, wherein the second time period is about 20 min to about 120 min.

16. The method of claim 1, wherein the processing cycle has a total duration of about 20 min to about 240 min.

17. The method of claim 1, wherein the first pressure is sufficient to maintain any water present in substantially liquid form.

18. The method of claim 1, wherein the processing cycle produces a product composition with an increased level of $C_5$ saccharides relative to a batch processing cycle without the redirecting, washing, removing, and repeating steps.

19. The method of claim 1, wherein a weight ratio of total water added during the method to dry biomass is less than 10.

20. The method of claim 1, wherein, prior to the forming, at least one of the first fresh biomass and the second fresh biomass is subjected to steaming.

21. A method for biomass hydrolysis to maximize sugar yields from the biomass comprising, in a processing cycle:
   forming a mixture comprising a first fresh biomass and a first wash liquor;
      optionally, wherein the first wash liquor comprises a wash liquor from a previous processing cycle;
   heating the mixture at a first temperature and a first pressure for a first time period, thereby forming a first liquid fraction and a first solid fraction
   redirecting at least a portion of the first liquid fraction from the first solid fraction,
      wherein the first liquid fraction comprises a product composition;
   washing the first solid fraction with fresh water;
      wherein the washing comprises heating the first solid fraction and the fresh water at a second temperature and a second pressure for a second time period, thereby forming a second wash liquor and a second solid fraction;
   removing at least a portion of the second wash liquor from the second solid fraction; wherein at least a portion of the first liquid fraction is collected; wherein the first temperature is at least about 110° C. and the second temperature is less than the first temperature; and
   repeating the processing cycle using a second fresh biomass in place of the first fresh biomass;
   wherein the method is directed toward maximizing sugar yields.

22. The method of claim 21, wherein the portion of the second wash liquor is used as at least a portion of the first wash liquor in the repeating step.

23. The method of claim 21, wherein the first wash liquor comprises a wash liquor from a previous processing cycle.

24. The method of claim 21, wherein liquid comprising biomass hydrolysate is combined with fresh water to form the first wash liquor.

25. The method of claim 21, further comprising:
   pressing the second solid fraction to obtain a third solid fraction and a third liquid fraction;
   wherein at least a portion of the third liquid fraction is used as at least a portion of the first wash liquor in the repeating step.

26. The method of claim 21, further comprising:
   subjecting the second solid fraction to further treatment selected from the group consisting of hydrothermal treatment, acid hydrolysis, enzymatic hydrolysis, solvent extraction, and combinations thereof.

27. The method of claim 26, wherein the further treatment comprises hydrothermal treatment, and the hydrothermal treatment comprises contacting the second solid portion with at least one fluid selected from the group consisting of supercritical fluid, near critical fluid, subcritical fluid, hot compressed water, and combinations thereof.

28. The method of claim 21, wherein at least one of the first fresh biomass and the second fresh biomass independently is selected from the group consisting of a cellulosic material, paper, cardboard, lignocellulosic material, municipal waste, municipal solid waste, manufacturing waste, food waste, agricultural residue, corn stover, sugarcane bagasse, grass, bark, dedicated energy crops, wood residue, sawmill and paper mill discards, hardwood, softwood, plastic, synthetic polymers, synthetic oligomers, natural polymers, natural oligomers, and combinations thereof.

29. The method of claim 21, wherein the product composition comprises $C_5$ saccharides selected from the group consisting of $C_5$ oligosaccharides, xylose, arabinose, lyxose, ribose, and combinations thereof.

30. The method of claim 29, wherein at least one of the first wash liquor and the second wash liquor has a concentration of $C_5$ saccharides which is about 5 times to about 10 times less than the concentration of the $C_5$ saccharides in the product composition.

31. The method of claim 21, wherein, in the product composition, a weight ratio of furfural to xylose is less than 0.4.

32. The method of claim 21, wherein the first temperature is about 110° C. to about 220° C.

33. The method of claim 21, wherein the second temperature is about 80° C. to about 190° C.

34. The method of claim 21, wherein the first time period is about 10 min to about 140 min.

35. The method of claim 21, wherein the second time period is about 20 min to about 120 min.

36. The method of claim 21, wherein the processing cycle has a total duration of about 20 min to about 240 min.

37. The method of claim 21, wherein the first pressure is sufficient to maintain any water present in substantially liquid form.

38. The method of claim 21, wherein the processing cycle produces a product composition with an increased level of $C_5$ saccharides relative to a batch processing cycle without the redirecting, washing, removing, and repeating steps.

39. The method of claim 21, wherein a weight ratio of total water added during the method to dry biomass is less than 10.

40. The method of claim 21, wherein, prior to the forming, at least one of the first fresh biomass and the second fresh biomass is subjected to steaming.

* * * * *